(12) United States Patent
McCabe

(10) Patent No.: US 9,737,685 B2
(45) Date of Patent: Aug. 22, 2017

(54) EXPANDABLE CATHETER

(75) Inventor: Tammy K. McCabe, Madison, AL (US)

(73) Assignee: Mac Catn, LLC, Madison, AL (US)

( * ) Notice: Subject to any disclaimer, the term of this patent is extended or adjusted under 35 U.S.C. 154(b) by 1134 days.

(21) Appl. No.: 13/570,172

(22) Filed: Aug. 8, 2012

(65) Prior Publication Data

US 2013/0204230 A1    Aug. 8, 2013

Related U.S. Application Data

(60) Provisional application No. 61/521,330, filed on Aug. 8, 2011.

(51) Int. Cl.
*A61M 25/00* (2006.01)
*A61M 25/06* (2006.01)

(52) U.S. Cl.
CPC .... *A61M 25/0023* (2013.01); *A61M 25/0043* (2013.01); *A61M 25/0662* (2013.01); *A61M 2025/0024* (2013.01)

(58) Field of Classification Search
CPC .......... A61M 25/0023; A61M 25/0043; A61M 25/0045; A61M 25/0662; A61M 2025/0024; A61M 2025/0025; A61M 2025/0062
See application file for complete search history.

(56) References Cited

U.S. PATENT DOCUMENTS

| | | | | |
|---|---|---|---|---|
| 3,789,852 A * | 2/1974 | Kim | .................. | A61B 17/3439 604/104 |
| 5,234,425 A * | 8/1993 | Fogarty | ................ | A61B 17/221 606/1 |
| 5,256,150 A * | 10/1993 | Quiachon | .......... | A61B 17/3462 604/164.02 |
| 5,320,611 A * | 6/1994 | Bonutti | .............. | A61B 17/0401 604/264 |
| 5,407,430 A * | 4/1995 | Peters | ............... | A61M 25/0043 604/104 |
| 5,460,170 A * | 10/1995 | Hammerslag | ...... | A61B 17/3439 600/201 |
| 6,616,678 B2 * | 9/2003 | Nishtala | ................ | A61M 29/02 604/104 |
| 8,900,191 B2 * | 12/2014 | Lenker | .............. | A61M 25/0662 604/101.04 |
| 2006/0135981 A1* | 6/2006 | Lenker | ............... | A61B 17/3439 606/191 |
| 2009/0240202 A1* | 9/2009 | Drasler | ............. | A61M 25/0023 604/164.03 |
| 2010/0324490 A1* | 12/2010 | Pini | ................... | A61M 25/0668 604/167.03 |
| 2011/0282156 A1* | 11/2011 | Lenker | ............... | A61B 17/3439 600/208 |
| 2012/0101510 A1* | 4/2012 | Lenker | ............ | A61B 17/12118 606/159 |
| 2012/0158033 A1* | 6/2012 | Deal | ..................... | A61M 29/00 606/191 |

* cited by examiner

*Primary Examiner* — Andrew Gilbert
(74) *Attorney, Agent, or Firm* — Lanier Ford Shaver & Payne PC

(57) ABSTRACT

A fluid delivery mechanism that has a substantially cylindrical sleeve and an actuator coupled to the sleeve for controlling a circumference of the sleeve.

9 Claims, 8 Drawing Sheets

A smaller gauge catheter would be necessary, e.g., a 22- or 24-gauge catheter. In such a scenario, the healthcare provider would be required to re-stick the patient with a new needle to deliver a smaller gauge catheter to a vein in order to effectively create a port through which the medicine could be delivered to the vein.

EXPANDABLE CATHETER

CROSS REFERENCE TO RELATED APPLICATIONS

This application claims priority to Provisional Patent Application U.S. Ser. No. 61/521,330, entitled "Vascular Expandable Catheter" and filed on Aug. 8, 2011 and Provisional Patent Application U.S. Ser. No. 61/528,755, entitled "Expandable Catheter" and filed on Aug. 29, 2011, which are both fully incorporated herein by reference.

BACKGROUND

Catheters are well known medical devices used to facilitate various medical procedures, such as diagnostic or delivery procedures. Catheter tubes are inserted into a body of a patient for various medical procedures. For example, a catheter may be used in performing diagnostic procedures such as removing a sample from a body site of a patient. Furthermore, a catheter may be inserted into an arm of the patient so that various fluids can be introduced to the patient's venous system.

Generally, a catheter has a tube portion which is relatively stiff axially and radially to allow proper placement of the catheter in the patient's body. The catheter tip is inserted into the skin, organ wall, etc. by use of a needle that is coupled to the catheter. Once the catheter has been inserted to a desired placement, e.g., in a vein In a particular cavity, etc, of an organ, the needle is removed leaving the end of the catheter (the tube portion) situated in the desire placement.

In this regard, catheters are to convey fluids into and out of body cavities besides veins. For example, catheters are often placed into arteries to measure blood pressure or remove arterial blood for analysis of gases reflecting lung function;

catheters are placed into the peritoneum (the space surrounded by the peritoneal membrane and external to organs in the abdomen) to perform peritoneal dialysis and remove fluids and toxins from the patient. And other catheters are placed into the fluid around the nervous system (cerebral spinal fluid) for removal of this fluid or administration of drugs, and into the subcutaneous space for administration of various drugs or fluids. Catheters are subject to infection and to other problems.

Depending upon the use and application of the catheter, the size of the catheter, i.e., the diameter of the tube, including the openings, varies. In this regard, catherers come in various sizes or "gauges," as it is termed in the art. In some applications, for example for the delivery of blood in transfusions, the catheter may need to be a 14- or 16-gauge catheter, and in the delivery of medicines to the venous system of a patient, the catheter mar need to be a 20- or 22-gauge catheter, Note that the smaller the diameter of the catheter, the larger the gauge.

Therefore, a 22-gauge catheter is smaller than a 14-gauge catheter. The greater the diameter, the more fluid that can be delivered through the catheter. To deliver large amounts of fluid, a healthcare provider uses a 14 or 16-gauge catheter. To administer medications, a healthcare provider uses an 18- or 20-gauge catheter.

If a catheter is initially inserter in a patient's vein through which to deliver blood, e.g., for a transfusion (where typically a 14- or 16-gauge catheter would be used), the same catheter cannot be used to also deliver needed medication. In this regard, to deliver the needed medication to the patient, a smaller gauge catheter would be necessary, e.g., a 22- or 24-gauge catheter. In such a scenario, the healthcare provider would be required to re-stick the patient with a new needle to deliver a smaller gauge catheter to a vein in order to effectively create a port through which the medicine could be delivered to the vein.

BRIEF DESCRIPTION OF THE DRAWINGS

The invention can be better understood with reference to the following drawings. The elements of the drawings are not necessarily to scale relative to each other, emphasis instead being placed upon clearly illustrating the principles of the invention. Furthermore, like reference numerals designate corresponding parts throughout the several views.

DETAILED DESCRIPTION

Figure 1:
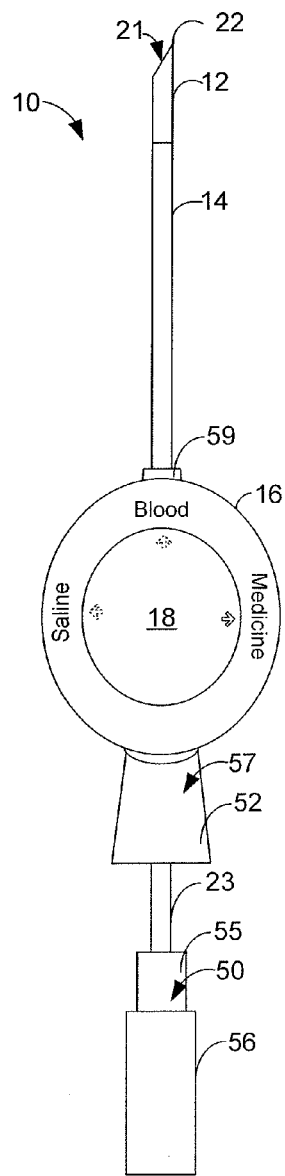
FIG. 1 is a plan view of a fluid delivery mechanism in accordance with an embodiment of the present disclosure.

FIG. 1 depicts a fluid delivery mechanism 10 in accordance with an embodiment of the present disclosure. The fluid delivery mechanism 10 comprises a needle 21 that is coupled to a needle actuation device 50. In addition, the fluid delivery mechanism 10 comprises a dial 16, which is attached to a plastic sheath 57.

The dial 16 may comprise various settings or indicators indicative of the size catheter to be used or type of substance to be delivered. In one embodiment, the dial 16 may have that indicators for "Blood," "Medicine," or "Saline."

In another embodiment, the dial 16 may have indicators for "16-gauge," "20-gauge," or "22-gauge," or "24-gauge." In such an embodiment, each indicator correlates to a particular size of catheter. Note that the settings illustrated are for exemplary purposes only. Other types of identifiers for the settings and other types of setting criteria may be used in other embodiments to indicate varying sizes of catheter diameters. As an example, the settings may be identified with gauge numbers, e.g., 16-, 20-, or 22-.

The needle actuation device 50 comprises a cylindrical sub-base 55 that is fixedly attached to a bottom protruding portion 23 of the needle 21. Further, the needle actuation device 50 comprises a handle 56.

In addition, the plastic sheath 57 comprises a closed end 59 that attaches to a hollow sleeve 14 in and through which the needle 21 is initially and removeably retained. The plastic sheath 57 further comprises an open-ended base 52. Where the closed end 59 attaches to the open-ended base 52 and inside the open-ended base 52 is a port to which tubing is attached that is connected to a fluid source.

During normal operation, a healthcare provider (not shown) inserts a tip-end 22 of the needle 21 through a patient's skin and through a wall of a vein (not shown) so that an opening (riot shown) in the tip-end 22 is contained within a vein or any other body structure or cavity to which a substance is to be delivered.

As the healthcare provider pushes the needle through the skin and into the vein, the healthcare provider also pushes the plastic sheath 57 into the vein. Thus, the hollow sleeve 14 travels with the needle 21 through the skin and into the wall of the vein where both the sleeve 14 and needle 21 are contained in the vein. Notably, the needle 21 is used in order to penetrate the skin and the vein and deposit the sleeve 14 in the vein when the needle 21 is removed.

Thus, once the needle 21 and the sleeve 14 are inserted through the wall of the vein, the needle 21 is then removed. In this regard, the healthcare provider slidably decouples the needle 21 from the plastic sheath 57. Once the tip-end 22 of the needle 21 is inserted through the wall of the vein, the healthcare provider slowly slides the needle actuation device 50 from the plastic sheath 57 such that the sleeve 14 remains in the vein and there is access to deliver fluids to the vein through the sleeve 14. In this regard, as noted herein, the needle 21 is coupled to the actuation device 50 and when the actuation device 50 is removed, the plastic sheath 57 is left with the sleeve 14 remaining in the vein.

Figure 2:
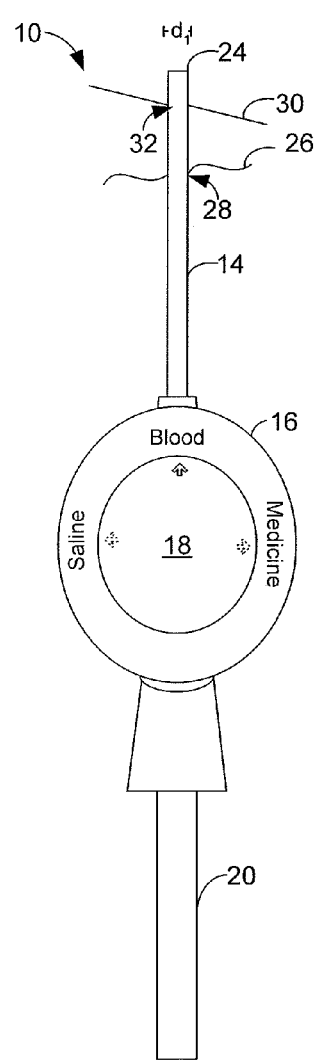
FIG. 2 is a plan view of the fluid delivery mechanism such as is depicted in FIG. 1 showing the needle removed and the catheter inserted in a vein.

FIG. 2 depicts the fluid delivery mechanism 10 after the sleeve 14 of the plastic sheath 57 has been inserted. In this regard, FIG. 2 depicts an end 24 of the sleeve 14 within an opening 32 of a vein 30 and through an opening 28 in skin 26. Note that the illustration is not necessarily accurately depicted. Specifically, the sleeve 14 would be aligned substantially parallel with walls of the vein 30. However, for simplicity, FIG. 2 simply shows the sleeve 14 inserted through the vein wall of the vein 30.

Figure 3:
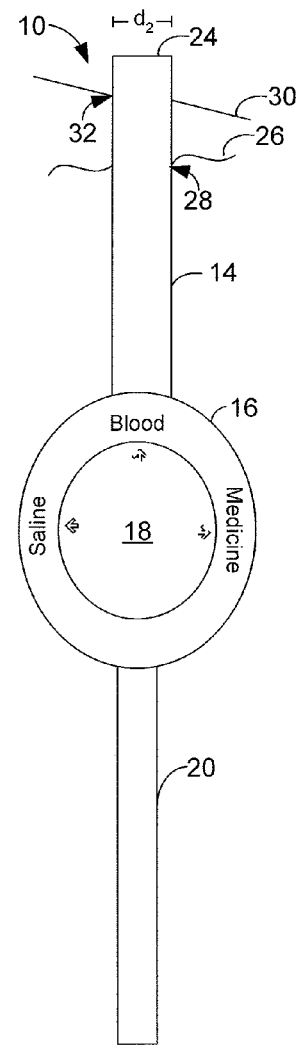
FIG. 3 is a plan view of the fluid delivery mechanism such as is depicted in FIG. 1 showing the catheter sleeve expanded.

The sleeve 14 is shown having a smaller diameter $d_1$ than the diameter $d_2$ of the sleeve 14 depicted in FIG. 3. Thus, the sleeve 14 may have a diameter that may effectively be used to deliver, e.g., medicine. Whereas, the sleeve 14 may be used, because it is larger, to deliver blood to the patient, e.g., for a transfusion. Note that while the sleeve 14 exhibits the diameter the arrow of the dial 16 is pointing to "Medicine."

During operation the sleeve 14 having the initial diameter $d_1$ may be initially inserted into the vein 30. The healthcare provider inserts tubing 20 through the open-ended base 52 and couples the tubing 20 to the port (not shown) within the open-ended base 52 so that the tubing 20 is in fluid communication with the sleeve 14.

After medicine is been delivered to the vein 30, a doctor may order that the patient undergo a transfusion. Instead of re-sticking the patient and inserting a differently sized catheter into the same or different vein, the healthcare provider may actuate (rotate) a knob 18 of the dial 16 so that the arrow points to "Blood."

When the healthcare provider rotates the knob 18, the fluid deliver device 10 expands the diameter $d_1$ of the sleeve 14 depicted in FIG. 2 to the diameter $d_2$ of sleeve 14 depicted in FIG. 3. Thus, the healthcare provider need not re-stick and insert a new catheter into the patient's body. Instead, the healthcare provider may simply actuate the knob 18, which increases the sleeve diameter and change the source of the fluid, e.g., a fluid bag attached to the tubing 20.

Figure 4:
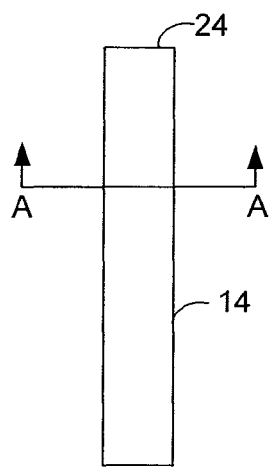
FIG. 4 is a plan view of a catheter sleeve of the fluid delivery mechanism such as is depicted in FIG. 1.

FIGS. 4-9 illustrate one embodiment for expanding and contracting the sleeve 14 of the plastic sheath 57. FIG. 4 depicts the sleeve 14 having the open end 24 that is inserted through the vein wall.

Figure 5:
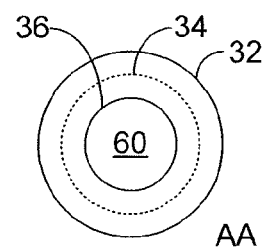
FIG. 5 cross-sectional view of the catheter sleeve such as is depicted in FIG. 2.

FIG. 5 depicts a cross-sectional view of the sleeve 14 of FIG. 4 taken along line AA. With respect to FIG. 5, in one embodiment, the sleeve 14 comprises three layers including a plastic outer layer 32, a plastic inner layer 36, and an expansion/contraction layer 34. FIG. 5 appears to depict the layers 32, 34, and 36 separated one from the other. However, this is shown in such a manner for illustrative purposes only. In one embodiment, the layers are attached one to the other so that there is no space between each of them. In one embodiment, the expansion/contraction layer 36 is embedded with the plastic layers 32 and 36.

Note that while three layers, including layer 32, 34, and 36 are shown, any number of layers may be used in other embodiments. For example, the sleeve 14 may have only two layers, including a plastic outer (or inner) layer and the expansion/contraction layer 34. In such an embodiment, the expansion/contraction layer 34 may be coupled to the plastic layer so that the expansion/contraction layer 24 is the outside layer or the inside layer.

The layers 32, 34, and 36 form a hollow tube. In this regard, the sleeve 14 comprises a hollow cavity 60 that enables fluid to travel through the port (not shown) in the plastic sheath 57, through the hollow cavity 60 and ultimately to the vein 30 (FIG. 2).

Figure 6:
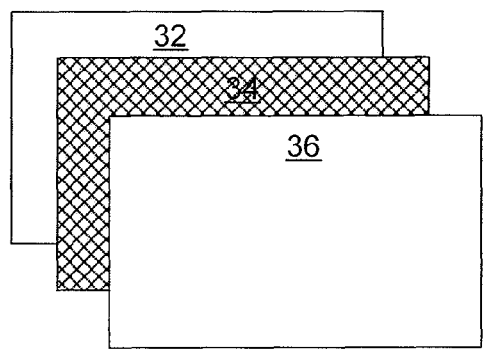
FIG. 6 depicts layer of the catheter sleeve such as is depicted in FIG. 5.

FIG. 6 illustrates the various layers, including 32, 34, and 36 that make up the sleeve 14. Notably, there is an inner plastic layer 36 and an outer layer 32. Embedded between the plastic layers 36 and 32 is the expansion/contraction layer 34.

As described hereinabove, in one embodiment, the inner layer 36 and the outer layer 32 are made out of a plastic material. In such an embodiment, the plastic is pliable and expandable and exhibits substantial rigidity so that it can be effectively inserted into the vein 30 (FIG. 2) and substantial flexibility so that the diameter of the sleeve 14 can be manipulates,e.g., expanded and contracted. Other materials and/or types of materials may be used in other embodiments of the sleeve 14.

Furthermore, in one embodiment, the expansion/contraction layer 34 is made of a strong metal material that is substantially strong to expand and/or contract the diameter of the sleeve 14. In one embodiment, the expansion/contraction layer 34 is made out of carbon nanotubes.

Carbon nanotubes are molecular-scale tubes of graphitic carbon with special characteristics. The carbon nanotubes are stiff and strong fibers known. As will be described further herein, the carbon nanotubes can be used to create the expansion/contraction layer 34 that is small enough to be embedded as a layer between the plastic layers 32 and 36 and strong enough that when expanded or contracted, the expansion/contraction layer 34 will in turn increase or decrease the diameter of the sleeve 14. Notably, the tensile strength of carbon nanotubes is 50X that of steel.

Figure 7:
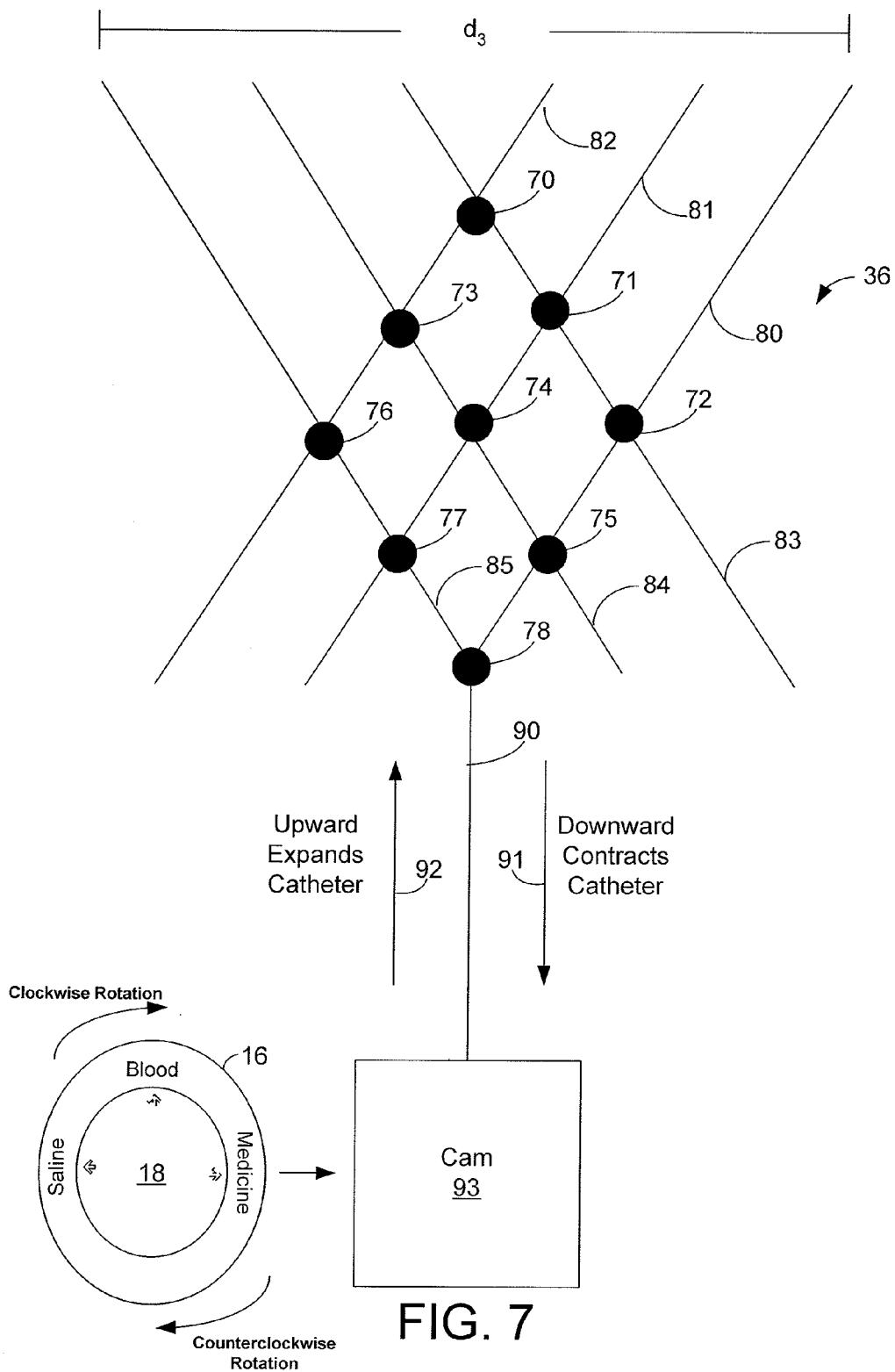
FIG. 7 is a diagram of a mesh layer of the catheter sleeve such as is depicted in FIG. 6 showing the mesh layer interface to a cam and a dial of the fluid delivery system such as is depicted in FIG. 1.

An exemplary structure of the expansion/contraction layer 36 is depicted in FIG. 7. In this regard, the expansion/contraction layer 36 comprises a plurality of links 80-82 that are oriented diagonally in one direction. In addition, the expansion/contraction layer 36 comprises another plurality of links 83-85 that are also oriented diagonally however in an opposite direction that the links 80-82. Each of the links 80-82 is connected to one of the other links 83-85 at various pivot points 70-78. As described hereinabove, the links 80-82 and 76-78 may be, made of carbon nanotubes. At least one of the pivot points 78 is connected to an arm 90 that may be a small strand of metal, also comprised of carbon nanotubes.

During operation, when the healthcare provider (not shown) rotates the knob 18 of the dial 16 in a clockwise direction, a cam 93 translates the clockwise rotation into a pulling force that acts on the arm 90. As the healthcare provider turns the knob 18 clockwise, from blood to medicine, the cam 93 pulls on the arm 90, which forces the pivot point 78 downward in a direction indicated by arrow 91. In turn, as the pivot point 78 is forced downward, each of the other pivot points 72-77 rotates causing the pivot points o physically move closer together, which forces the plastic layers 32 and 36 in which the expansion/contraction layer 24 is embedded to contract. Thus, the diameter of the sleeve 14 decreases.

On the other hand, as the healthcare provider turns the knob 18 counterclockwise, from medicine to blood, the cam 93 pushes on the arm 90 upward. When the arm 90 is pushed upward, the force pushes the pivot point 78 upward in a direction indicated by arrow 92. In turn, as the pivot point 78 is forced upward, each of the other pivot points 72-77 rotates causing the pivot points to physically move away from each other, which forces the plastic layers 32 and 36 in which the expansion/contraction layer 24 is embedded to expand. Thus, the diameter of the sleeve 14 increases.

Figure 8:
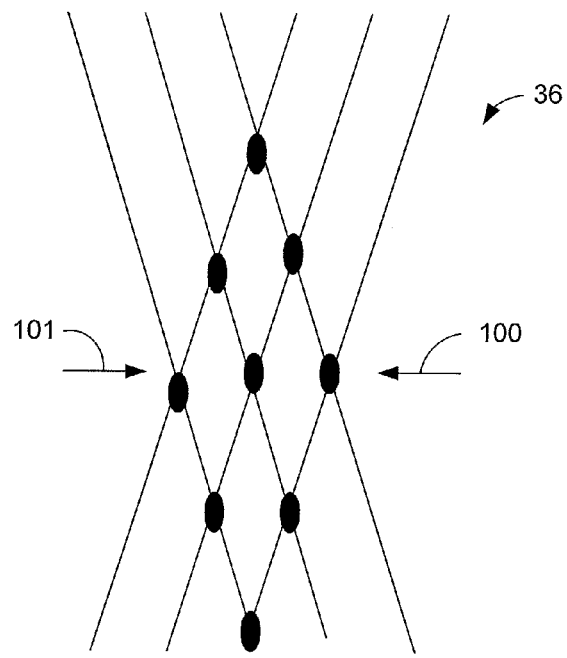
FIG. 8 is a diagram of the mesh layer such as is depicted in FIG. 7 in a contracted state.

FIG. 8 depicts the expansion/contraction layer 34 when the knob 18 has been actuated in a clockwise direction. The arrows 100 and 101 indicate that the pivot points move closer together, which causes the plastic layers 32 and 36 in which the expansion/contraction layer 34 is embedded to contract. As the plastic layers 32 and 36 contract, the diameter of the sleeve 14 decreases.

Figure 9:
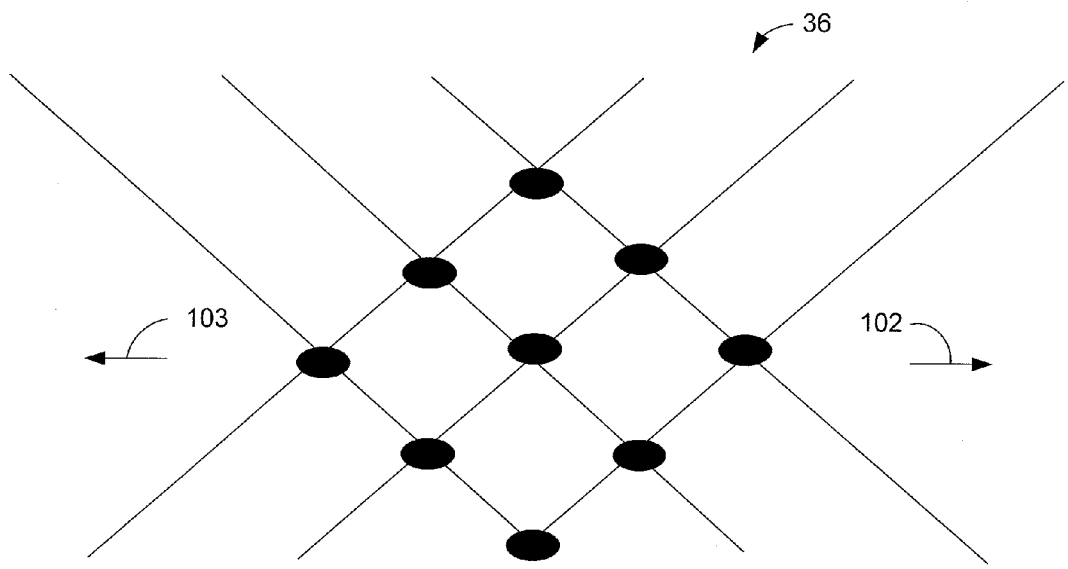
FIG. 9 is a diagram of the mesh layer such as is depicted in FIG. 7 in an expanded state.

FIG. 9 depicts the expansion/contraction layer 34 when the knob 18 has been actuated in a counterclockwise direction. The arrows 102 and 103 indicate that the pivot points move apart, which causes the plastic layers 32 and 36 in which the expansion/contraction layer 34 is embedded to expand. As the plastic layers 32 and 36 expand, the diameter of the sleeve 14 increases.

Figure 10:
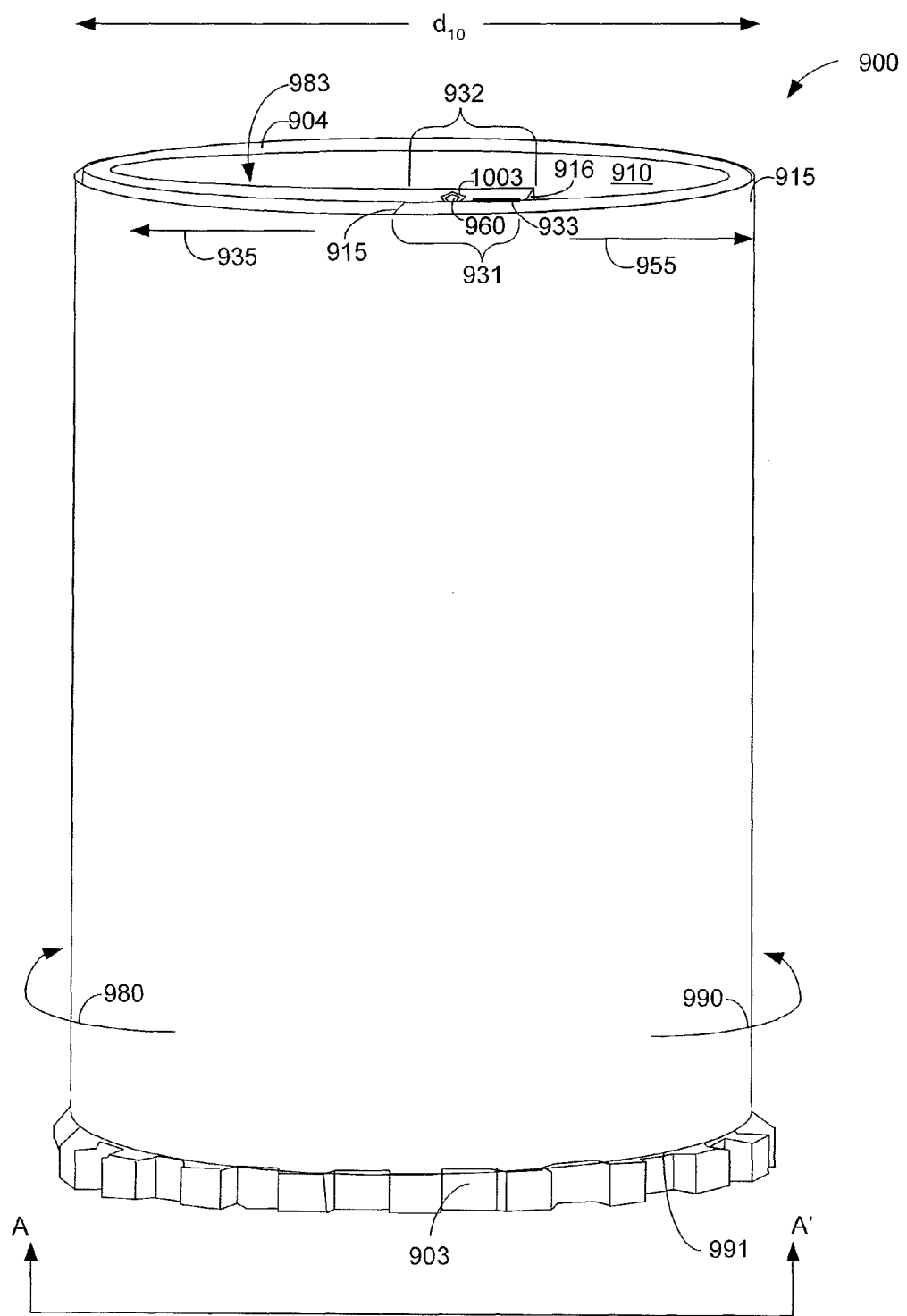
FIG. 10 is a plan view of an exemplary catheter sleeve in accordance with an embodiment of the present disclosure.
Figure 11:
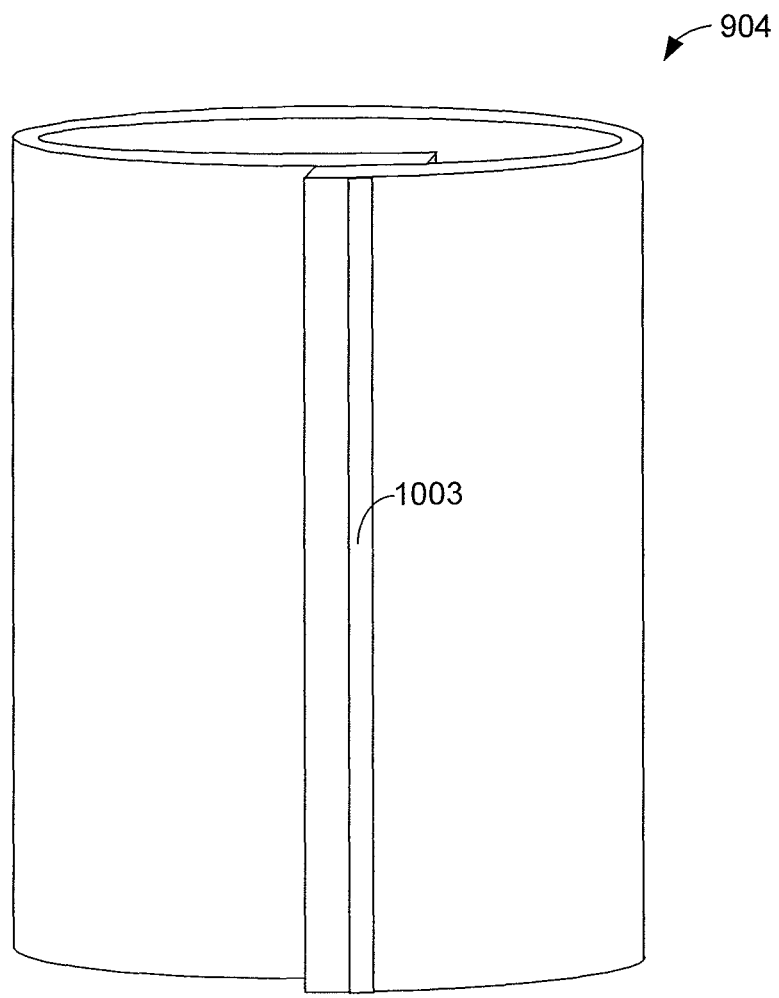
FIG. 11 is a plan view of an exemplary catheter inner layer such as is depicted in FIG. 10.
Figure 12:
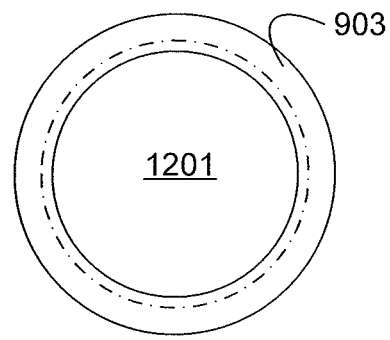
FIG. 12 is a cross-sectional bottom view taken along A-A' in FIG. 10.

FIGS. 10-12 illustrate another embodiment in which the catheter (sleeve 14 (FIG. 1)) of the fluid delivery device 10 (FIG. 1) can be contracted and expanded. In this regard, FIG. 10 depicts a sleeve 900 that is inserted through a vein wall as described hereinabove with reference to FIGS. 1-3 such that fluid may exit the sleeve 900 through an opening 910 of a cylindrical cavity 983 formed by the sleeve 900.

In this regard, a needle (not shown) is initially protruding from the opening 910 and once the sleeve 900 is inserted through the vein wall, the needle is removed leaving the opening 910 for delivery of fluids to the vein. Note that the sleeve 14 forms the opening 910 through which fluids can flow and be delivered to the vein.

The sleeve 900 comprises a circular inner layer 904 that is not connected end-to-end, i.e., not contiguous. In this regard, the inner layer 904 comprises two ends including end 915 and end 916. The ends 915 and 916 are interfaced and create the opening 910. In addition, end 915 overlaps end 916 such that an outside section 931 of the inner layer 904 overlaps an inside section 932 of the inner layer 904. Notably, there is an intersection area 933 (indiscernible gap) between the section 931 and 932.

In one embodiment of the intersection 933, section 931 is slidably coupled to section 932. In this regard, sections 931 and 932 are freely movable with respect to one another. Thus, when the section 931 is forced in a direction indicated by arrow 935, the diameter $d_{10}$ (and hence the circumference; of the opening 910 decreases.

In one embodiment, a lubricant (not shown) may be injected or applied between the sections 931 and 932. Thus, if a force pulls the outside section 931 in the direction indicated by arrow 935, the sections 931 and 932 more easily move with respect o one another. As the outside section 931 moves in the direction indicated by arrow 935, the diameter $d_{10}$ decreases. Also, as the outside section 931 moves in a direction indicated by 955, the diameter $d_{10}$ increases, in addition, the sleeve 900 comprises a circular outer layer 915. The circular outer layer 915 may be comprised of any type of plastic or metal material known in the art or future-developed, such as, for example, silicone or polyurethane.

In one embodiment, the outer layer 915 is fixedly coupled to the inner layer 904. In the embodiment shown in FIG. 10, the outer layer 915 comprises an elongated protrusion 960 that runs the length of the outer layer 915. Correspondingly, the inner layer 904 comprises a channel 1003 (shown in more detail in FIG. 11) that runs the length of the inner layer 904.

In another embodiment, the sleeve may not comprise the protrusion 960 and channel 1003 combination. Instead, a strip of adhesive may e used to fixedly couple the outer layer 915 to the inner lay 904.

Note that any type of method may be used to fixedly couple the outer layer 915 to the inner layer 904. The protrusion/channel coupling and the adhesive strip are described and shown for exemplary purposes only.

FIG. 11 depicts the inner layer 904 having the keyed channel 1003 formed in a surface 1020 of the inner layer 904, in such an embodiment, the outer layer 915 (FIG. 10) comprises the protrusion 960 (FIG. 10) that is keyed to the keyed channel 1003. To couple the outer layer 915 to the inner layer 904, the outer layer 915 is slid over the inner layer 904 while the protrusion 960 is slidably coupled to the channel 1003.

With respect to FIG. 10, as described hereinabove, in one embodiment the outer layer 915 is fixedly coupled to the inner layer 904. However, the outer layer 915 is contiguous, whereas the inner layer 904 can expand and contract as end 915 is moved in the directions indicated by arrows 935 and 955, respectively.

In one embodiment, sections 931 moves while the section 932 remains static thereby decreasing the diameter $d_{10}$. In another embodiment, sections 931 moves and section 932 moves in the opposite direction thereby decreasing the diameter $d_{10}$. Accordingly, when section 931 moves in the direction indicated by arrow 955, the diameter $d_{10}$ increases.

Because the outer layer 915 is fixedly coupled to the inner layer 904 at 912 and the end 915 may more in one direction and the other end 916 move in the other direction, if the outer layer 915 is twisted (or turned) Ill a direction indicated by arrow 980, the end 915 moves in the direction indicated by reference arrow 935, and the diameter $d_{10}$ (or circumference) of the inner layer 904 decreases.

If the outer layer 915 is twisted (or turned) in a direction indicated by reference arrow 900, the end 915 moves in the direction indicated by reference arrow 955, and the diameter $d_{10}$ for circumference) of the inner layer 904 increases.

In one embodiment, a gear 903 is coupled to a bottom 991 of the outer layer 915. The gear 903 may be any type of gear known in the art or future-developed. It may be trade of plastic, metal, or any other type of material known in the art or future-developed. The gear 903 is fixedly coupled to the bottom 991 of the outer layer 915 such that if the gear 903 is rotated, the outer layer 915 rotates also.

FIG. 12 depicts a cross-sectional bottom view of the sleeve 900 (FIG. 10) taken along A-A'. Notably, the gear 903 is fixedly coupled o the bottom 991 (FIG. 10) of the sleeve 900, and the center of the gear 903 is opened. Thus, the gear 903 forms the opening 1201. Therefore, fluids may flow through the opening 1201 into the channel (not shown) created by the inner layer 904 (FIG. 10) and out the opening 910 (FIG. 10) of the sleeve 900.

Figure 13:
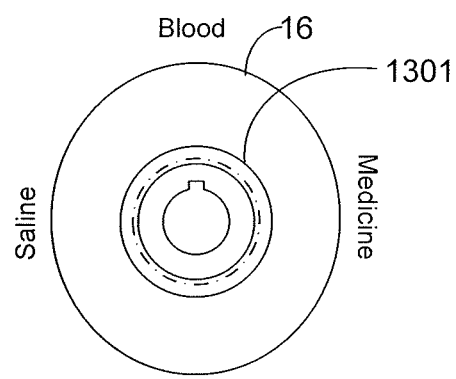
FIG. 13 is a backside view of an exemplary dial such as is depicted in FIG. 1.
Figure 14:
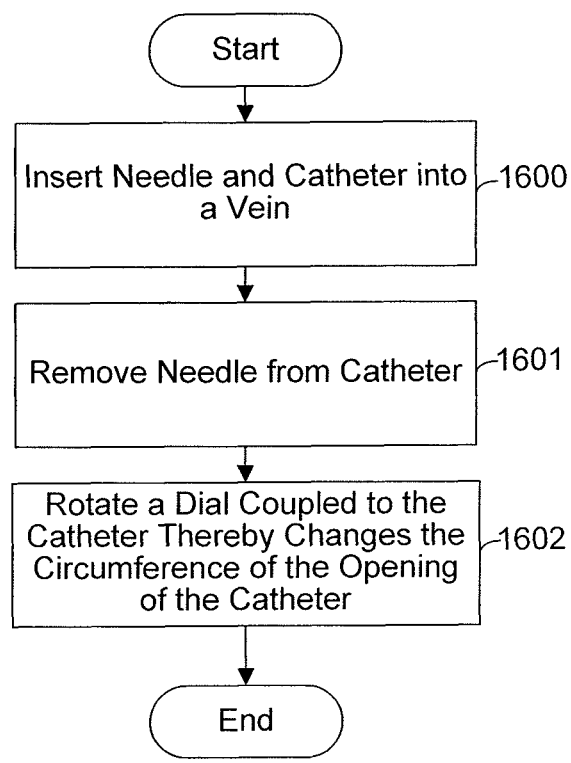
FIG. 14 is a flowchart depicting an exemplary method in accordance with an embodiment of the present disclosure.

FIG. 13 is a backside of an exemplary dial such as is depicted in FIG. 1. The exemplary dial 16 further comprises a gear 1301. The dial 16 is coupled to the sleeve 900 such that the gear 1301 interfaces with the gear 903. In one embodiment, the gear 1301/gear 903 arrangement is such that rotational turning of the dial 16 rotates the gear 1301, which is interfaced and coupled to the gear 903. As the gear 1301 rotates, such rotation causes angularly displaced rotation in the gear 903. As gear 903 rotates in a direction based upon actuation of the dial 16, the outer layer 915 rotates thereby increasing or decreasing the diameter d10 (FIG. 10) of the sleeve 900.

What I claim is:

1. A fluid delivery mechanism, comprising:
   a substantially cylindrical catheter configured for containing a needle and for insertion into a patient's vein, wherein the catheter comprises a mesh layer comprising a plurality of pivot points coupling a plurality of links and the links are expandable and contractible at the pivot points;
   a cam coupled to the plurality of pivot points, wherein each of the plurality of pivot points are coupled to an arm and each arm is coupled to the cam; and
   dial indirectly coupled to the plurality of pivot points via the cam and configured to rotate about an axis perpendicular to a longitudinal axis of the catheter, such that when the dial is rotated the cam is configured to translate rotation about the perpendicular axis of the dial into a straight pushing or pulling force parallel to the longitudinal axis which acts upon each arm, to expand or contract the mesh layer for controlling a circumference of the catheter, the diameter of which is based upon a circumference of the patient's vein and the medication to be delivered to the patient's vein.

2. The fluid delivery mechanism of claim 1, wherein rotation of the dial changes the circumference of the catheter based upon the amount of rotation of the dial thereby controlling an amount of medication delivered to the patient's vein.

3. The fluid delivery mechanism of claim 1, wherein the sleeve further comprises an inner layer coupled to an internal surface of the mesh layer and an outer layer coupled to an external surface of the mesh layer.

4. The fluid delivery mechanism of claim 1, wherein the catheter further comprises an inner layer and an outer layer.

5. The fluid delivery mechanism of claim 4, wherein the inner layer forms a cylindrical cavity and the inner layer comprises a first end and a second end which are not contiguous.

6. The fluid delivery mechanism of claim 1, wherein each arm is a strand of metal.

7. The fluid delivery mechanism of claim 6, wherein the metal is comprised of carbon nanotubes.

8. A fluid delivery method, comprising:
   inserting a needle coupled to a catheter into a patient's vein, wherein the catheter comprises a mesh layer comprising a plurality of pivot points coupling a plurality of links and the links are expandable and contractible at the pivot points; and
   removing the needle from catheter; and
   controlling a circumference of a cylindrical cavity of the catheter via dial indirectly coupled to at least one of the pivot points via a cam directly coupled to the plurality of pivot points via a plurality of arms, the dial rotating about an axis perpendicular to longitudinal axis of the catheter, such that when the dial is rotated, the cam translates rotation about the perpendicular axis of the dial into a straight pushing or pulling force in parallel with the longitudinal axis that acts upon the arm to expand or contract the mesh layer thereby controlling the circumference of the catheter based upon a circumference of the patient's vein and medication to be delivered to the patient's vein.

9. The fluid delivery method of claim 8, further comprising rotating the dial and changing the circumference of the catheter based upon the amount of rotation.

\* \* \* \* \*